US008074640B2

(12) United States Patent
Davies et al.

(10) Patent No.: US 8,074,640 B2
(45) Date of Patent: Dec. 13, 2011

(54) AROMA DISPENSING DEVICE

(75) Inventors: David Neville Davies, Oxford (GB); Alastair Bruce Pirrie, Oxford (GB); Ronald Alan Coffee, Haslemere (GB)

(73) Assignee: Battelle Memorial Institute, Columbus, OH (US)

( * ) Notice: Subject to any disclaimer, the term of this patent is extended or adjusted under 35 U.S.C. 154(b) by 1641 days.

(21) Appl. No.: 10/539,487

(22) PCT Filed: Dec. 18, 2003

(86) PCT No.: PCT/GB03/05556
§ 371 (c)(1),
(2), (4) Date: Apr. 14, 2006

(87) PCT Pub. No.: WO2004/054627
PCT Pub. Date: Jul. 1, 2004

(65) Prior Publication Data

US 2006/0261179 A1 Nov. 23, 2006

(30) Foreign Application Priority Data

Dec. 18, 2002 (GB) .................................. 0229493.2

(51) Int. Cl.
*A61M 15/00* (2006.01)
*B05B 17/06* (2006.01)

(52) U.S. Cl. ..................... 128/200.14; 239/34; 239/690; 239/704; 128/200.16; 128/203.12

(58) Field of Classification Search .......... 239/690–708; 128/200–208
See application file for complete search history.

(56) References Cited

U.S. PATENT DOCUMENTS

| | | | | |
|---|---|---|---|---|
| 4,095,596 | A * | 6/1978 | Grayson | 128/203.21 |
| 4,228,961 | A * | 10/1980 | Itoh | 239/698 |
| 4,581,675 | A * | 4/1986 | Kelly | 361/228 |
| 4,962,885 | A * | 10/1990 | Coffee | 239/3 |
| 5,267,555 | A * | 12/1993 | Pajalich | 128/200.14 |
| 5,337,963 | A * | 8/1994 | Noakes | 239/690 |
| 5,655,517 | A * | 8/1997 | Coffee | 128/203.12 |
| 6,457,470 | B1 | 10/2002 | Coffee | |
| 6,602,475 | B1 * | 8/2003 | Chiao | 422/124 |
| 6,684,879 | B1 * | 2/2004 | Coffee et al. | 128/200.14 |

* cited by examiner

*Primary Examiner* — Len Tran
*Assistant Examiner* — James Hogan
(74) *Attorney, Agent, or Firm* — Stevens & Showalter LLP

(57) ABSTRACT

A housing has a dispensing outlet (400) and contains: a liquid supplier (7) for supplying liquid containing at least one volatile component to a liquid outlet (7*a*); an electric field provider (41, 42, 7) for causing liquid issuing from the liquid outlet to provide electrically charged droplets from which at least a part of the at least one volatile component evaporates to produce vapour; a collection receptacle (92) for collecting electrically charged droplets to inhibit the electrically charged droplets from passing through the dispensing outlet; an attraction electrode (91) for attracting electrically charged droplets into the collection receptacle (90); and a flow director (95) for directing vapour away from the collection receptacle (92) and towards the dispensing outlet (400).

32 Claims, 12 Drawing Sheets

FIG. 14
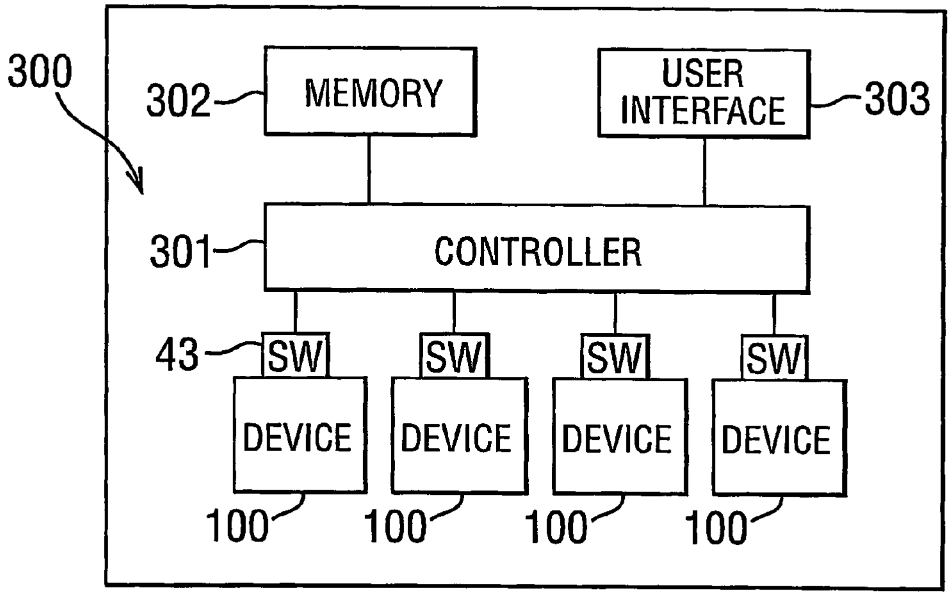
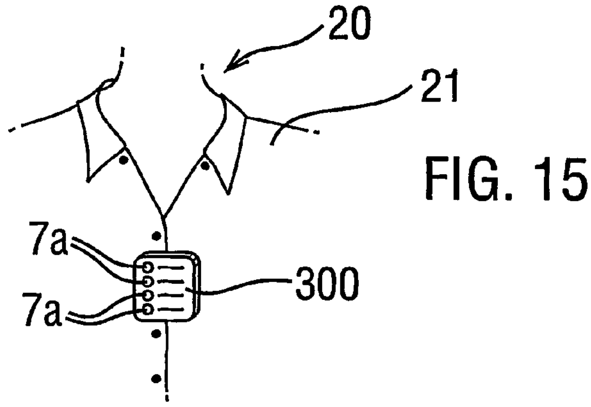
FIG. 15
FIG. 16
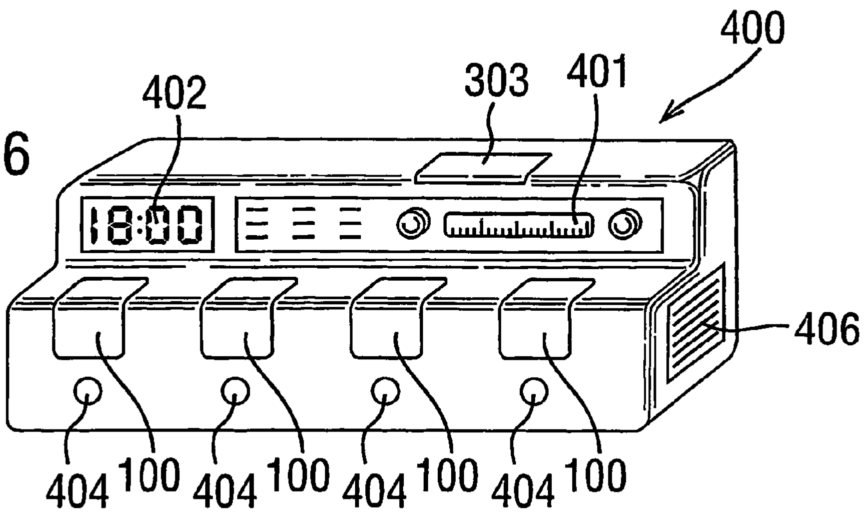

AROMA DISPENSING DEVICE

This invention relates to a device for dispensing an aroma or aromas.

There are various known techniques for dispensing or dispersing aromas or olfactory stimulants. For example, aromatic oils are often dispersed by application of heat to an evaporation surface. Aroma dispensing devices that work in this manner include the Ambi-Pur (Trade Mark) manufactured by the Sara Lee Corporation, light bulb oil reservoirs and aromatic candles. The application of heat to an aromatic oil may, however, detrimentally affect the aroma being dispensed. Also, where the aroma dispensing device comprises an aromatic candle, the vapour molecules carrying the aroma are often denatured or oxidized in the candle flame, reducing the intrinsic or "natural quality" of the fragrance. Other aroma dispensing devices rely on the use of a propellant or aerosol to enable dispersion. However, propellant or aerosol may detrimentally affect the aroma being dispensed.

In the conventional aroma delivery devices described above, it is difficult to control precisely delivery of the aroma. For example, in the case of an aromatic candle or other aroma delivery device that operates by using heat causing evaporation, some degree of evaporation will continue after the candle has been blown out or the device has been switched off. Also, aerosol cans and pump sprays produce large droplets which rapidly fall under gravity and settle, also resulting in a continuous or lingering aroma which may degrade with time.

In one aspect the present invention provides an aroma delivery device that avoids or at least reduces adverse effects on the aroma resulting from the manner in which the aroma is delivered.

In one aspect the present invention provides an aroma delivery device that enables good control over the delivery of the aroma so enabling, for example, precise switching on or off of the aroma and or precise targeting of the aroma enabling delivery or transmission of an aroma to a whole room of people or to an individual.

In one aspect, the present invention provides an aroma delivery device comprising at least one reservoir of aroma providing liquid coupled to a liquid supply outlet, electric field generating means for subjecting liquid at the liquid supply outlet to an electric field to cause comminution of liquid issuing from the liquid supply outlet so as to dispense aroma vapour or droplets carrying the aroma, electrical discharge means for at least partially discharging the droplets and control means for controlling the electric field generating means so as to control whether or not aroma carrying droplets are dispensed.

Any form of electric field effect technology that causes the liquid to be comminuted or broken up into droplets by electrical means may be used.

In an embodiment, liquid emerging from a liquid outlet is comminuted by an electric field in a process sometimes referred to as electrohydrodynamic comminution which is described in, for example, GB-A-1569707, the whole contents of which are incorporated herein by reference.

In one aspect the present invention provides an aroma delivery device comprising a supply of at least one aroma providing liquid; means for subjecting liquid issuing from the liquid supply to an electric field sufficient to cause comminution of the liquid to produce liquid droplets; electrical discharge means for at least partially electrically discharging the droplets; and means for adjusting the current voltage characteristics of the electric field generating means so as to retain the performance of the electric field whilst producing higher discharge currents from the discharge means.

An aroma delivery device embodying the invention enables good control over the supply of the aroma because, when the control means switches off the electric field generating means, comminution of the liquid and thus dispersal of aroma carrying droplets is stopped so that no further aroma above the threshold at which it is detectable by a human nose is delivered. Therefore, a clean aroma "signal" can be provided.

In one aspect, the present invention provides a method for generating and controlling the emission of an aroma or olfactory stimulant into a space in a fashion that offers control over and accuracy of time of emission and intensity of smell while avoiding or at least reducing emission of droplets of aromatic oils, particularly in the respirable size range, to avoid or at least reduce the generation of unwanted oil residues on surfaces near to the point of aerosol generation, thereby ensuring continuous efficient operation.

A device embodying the invention may be used for delivering aromas with electronic media such as television, virtual reality programs, compact discs etc.

An embodiment of the present invention provides a liquid reservoir containing bulk liquid aroma to be sprayed and connected to a capillary nozzle. By generating an electric field at the tip of the nozzle, the issuing bulk liquid is comminuted into electrically charged liquid droplets. This massive increase in the liquid's specific surface area causes a very rapid evaporation of scented vapour in the immediate vicinity. This scented vapour is rapidly diffused into space, assisted by an airflow (for example provided by a pump), which is directed through the droplets in flight. A collection counter-electrode is located to collect all the electrically charged liquid droplets by a combination of inertia and electric field forces. In one example, the collection electrode comprises an agent, such as activated charcoal, to absorb the aroma as it lands. In another example, the collection electrode targets the electrically charged aroma spray such that it subsequently drips or flows into a collection reservoir with minimal opportunity to release. In this way, the device is able to switch on and off an aroma, while also collecting the by-products of spraying. There also exists an opportunity to recycle those by-products for repeated use.

Embodiments of the present invention will now be described, by way of example, with reference to the accompanying drawings, wherein.

Figure 9A:
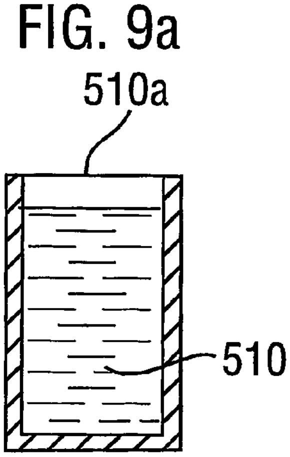
Figure 9B:
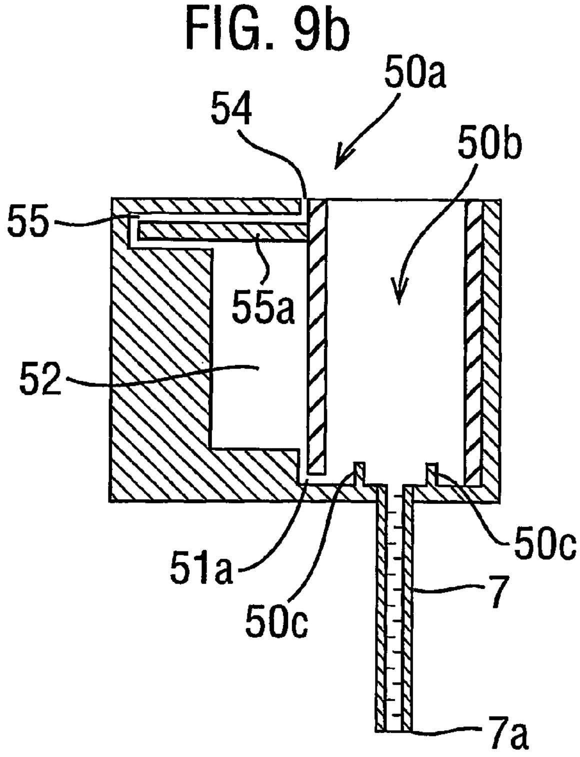
Figure 10:
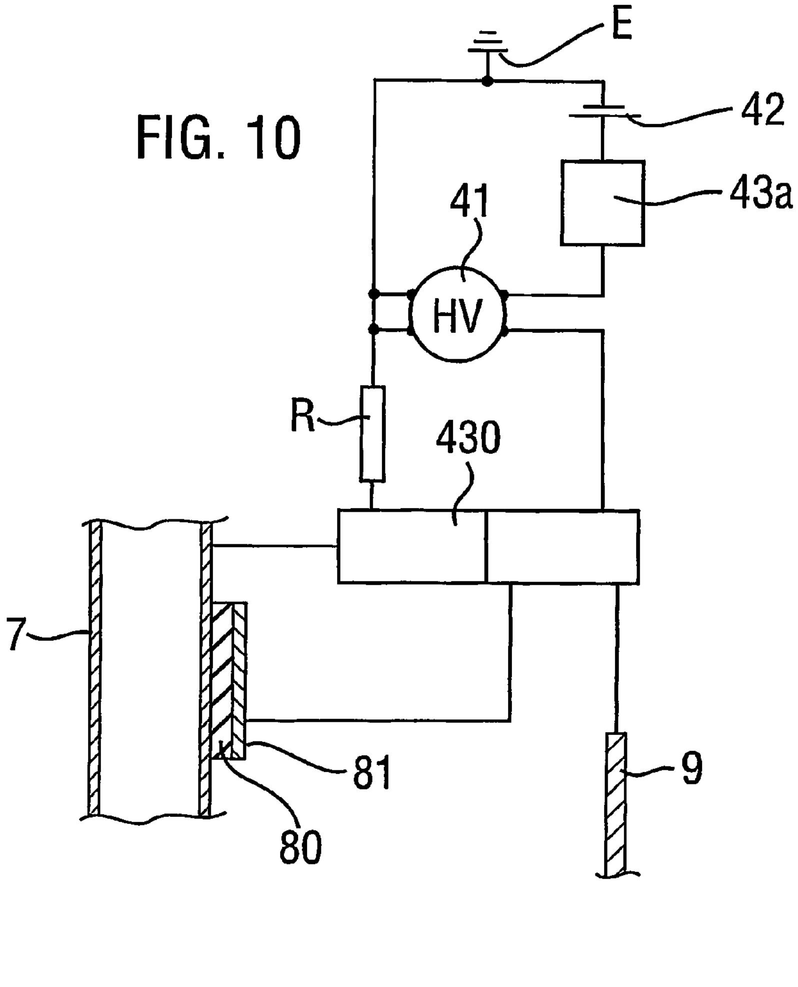
Figure 11A:
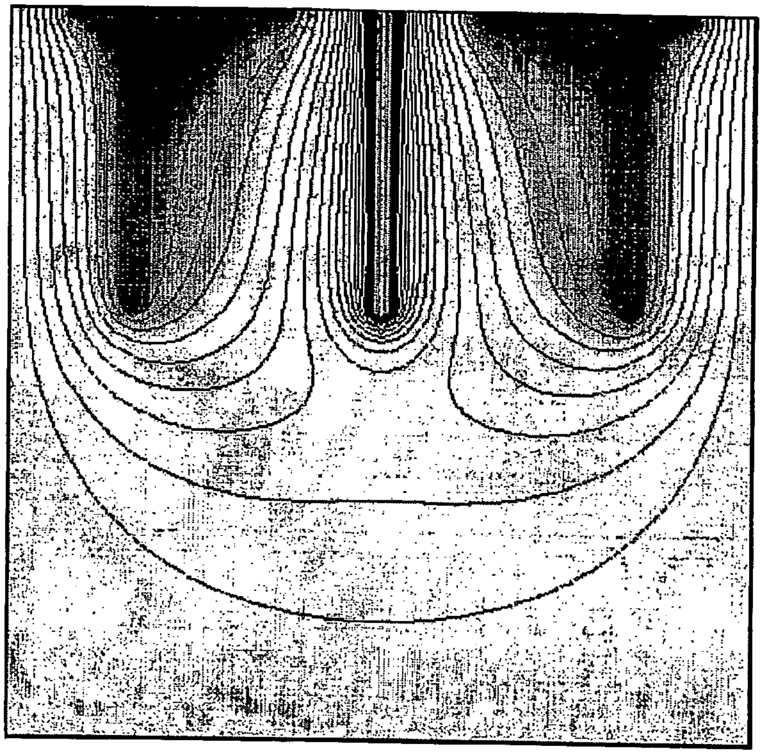
Figure 11B:
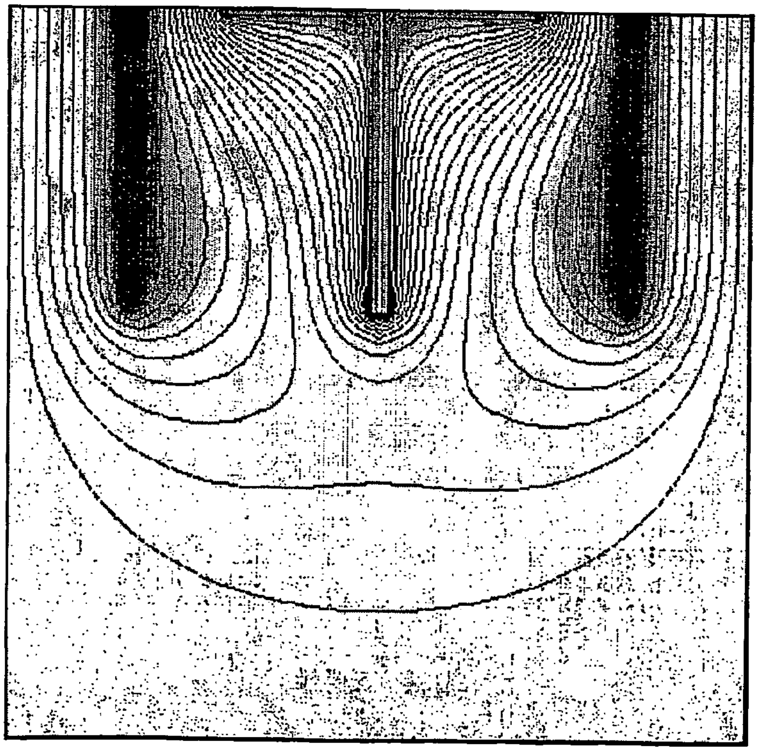
Figure 12:
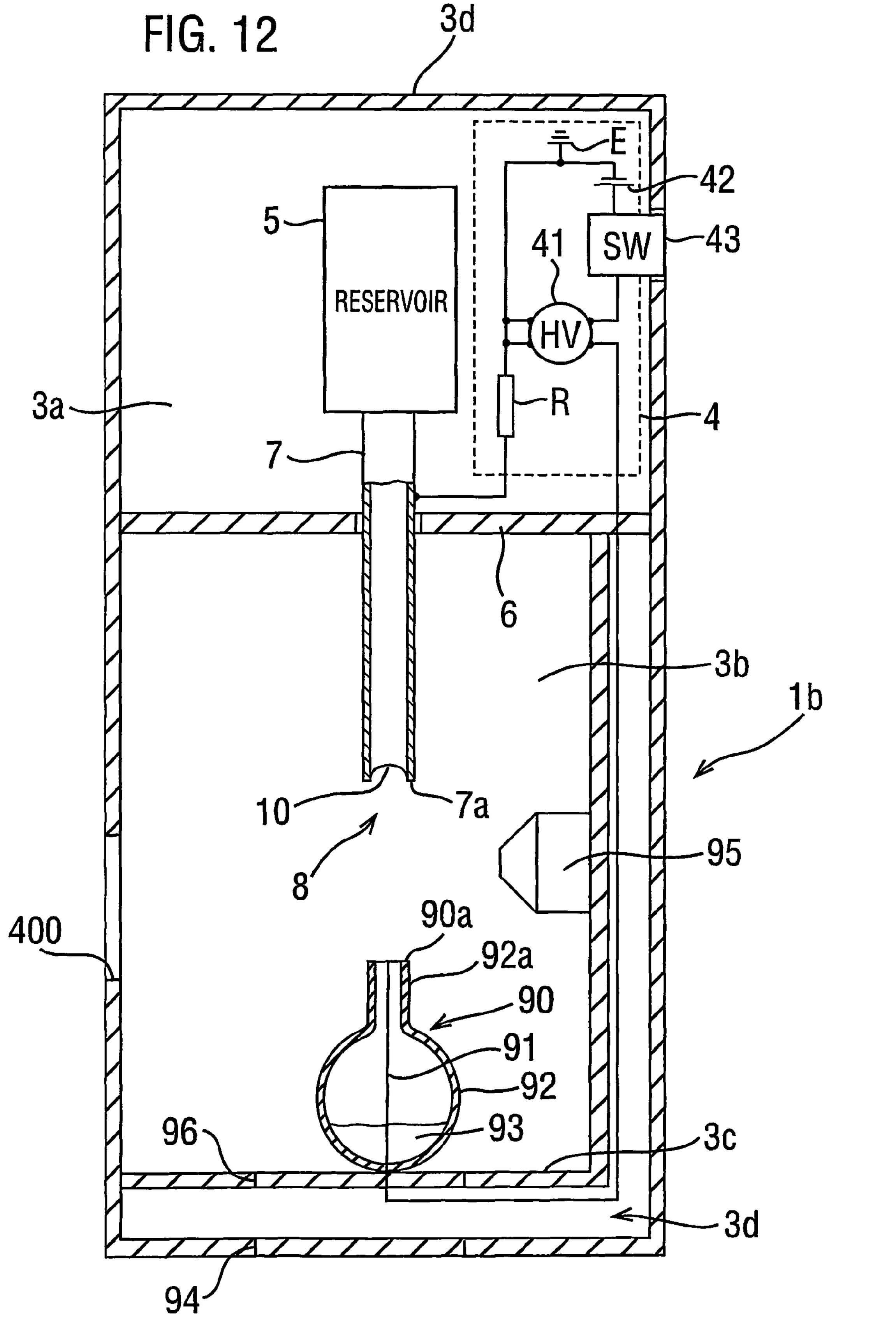
Figure 13:
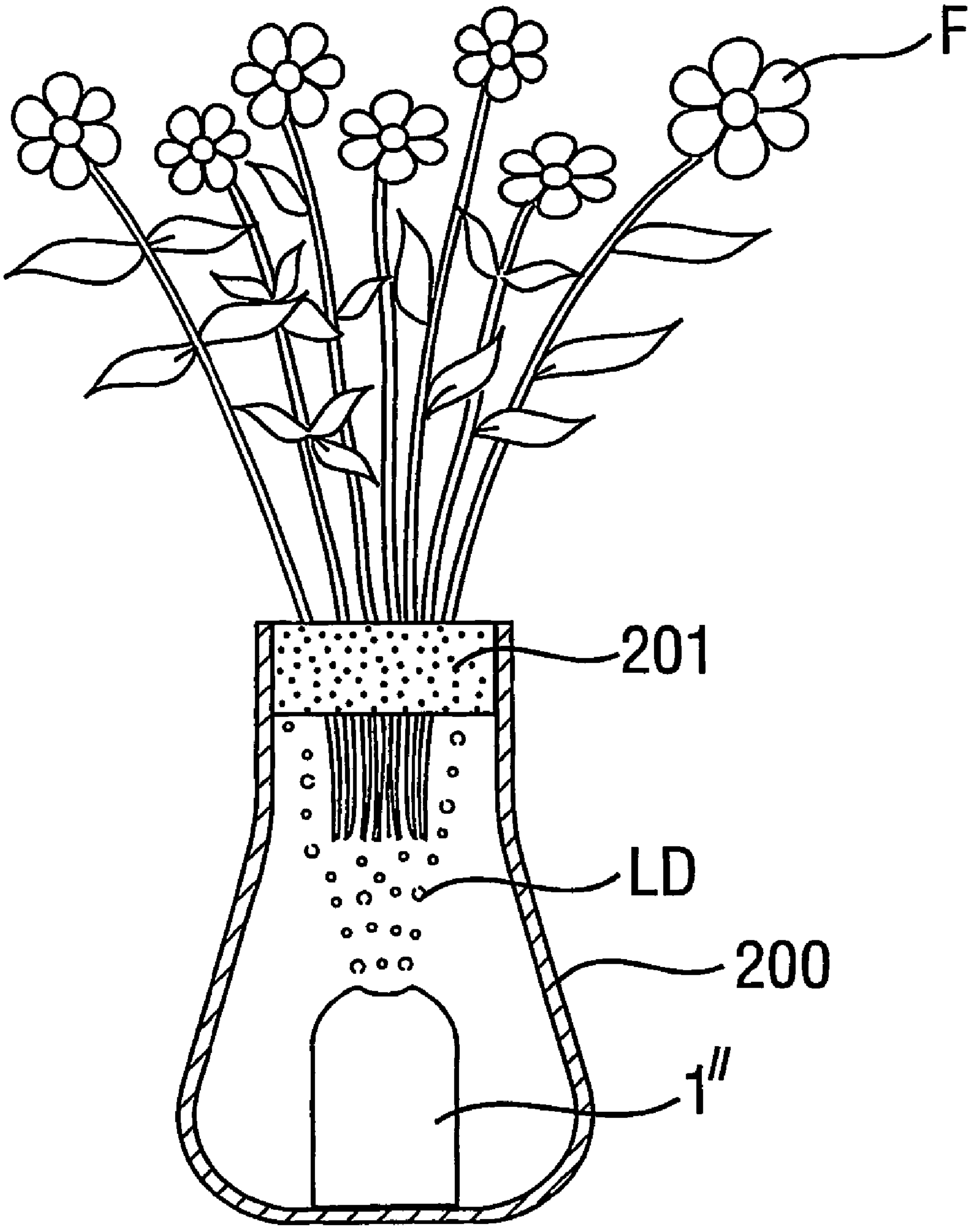
Figure 14A:
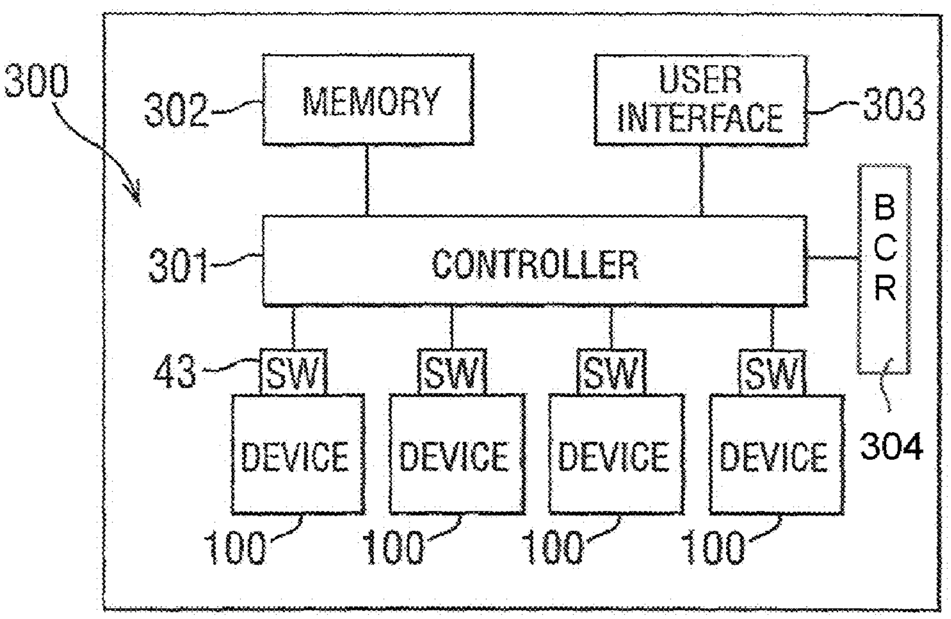
Figure 14B:
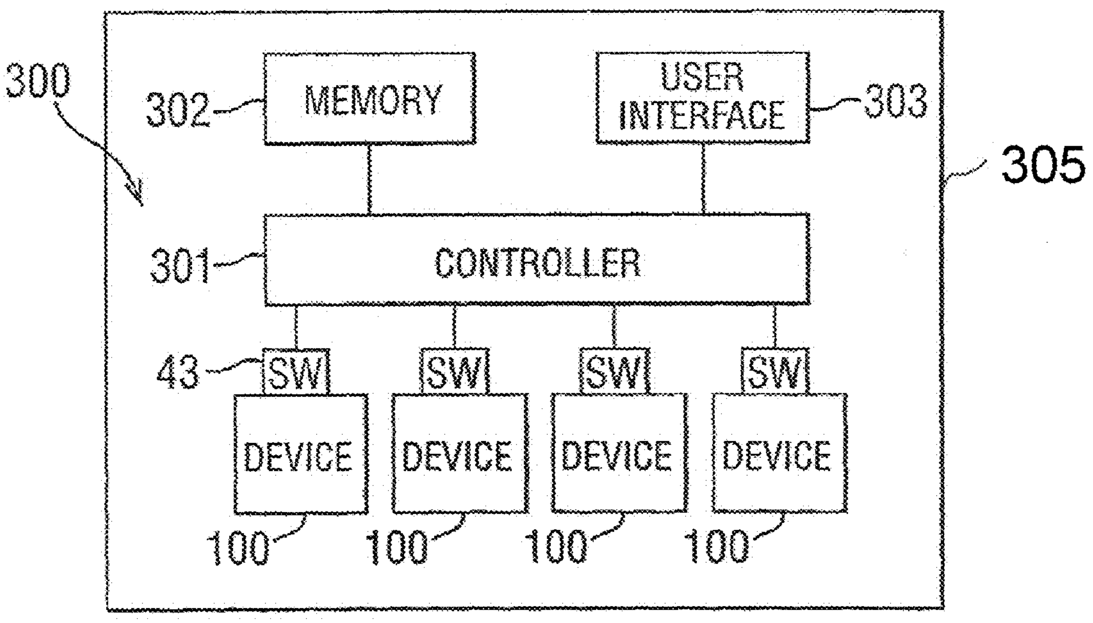

FIGS. 9*a* and 9*b* show, respectively, a replaceable liquid chamber and a modified liquid reservoir for receiving that replaceable liquid chamber;

FIG. 10 shows a diagrammatic view illustrating a further modification of a device embodying the invention;

FIGS. 11*a* and 11*b* show electric field diagrams;

FIG. 12 shows a diagrammatic part-sectional view of another embodiment of a device in accordance with the present invention;

FIG. 13 shows a diagrammatic part sectional view of an artificial flower arrangement incorporating a device embodying the present invention;

FIG. 14 shows a block diagram of apparatus embodying the invention incorporating one or more devices embodying the invention;

FIG. 14A illustrates in block diagram form an aroma delivery apparatus including a barcode reader;

FIG. 14B illustrates in block diagram form an aroma delivery apparatus provided in a vehicle;

FIG. 15 illustrates a user wearing apparatus embodying the invention; and

FIG. 16 shows a diagrammatic perspective view of a clock radio embodying the present invention.

Figure 1:
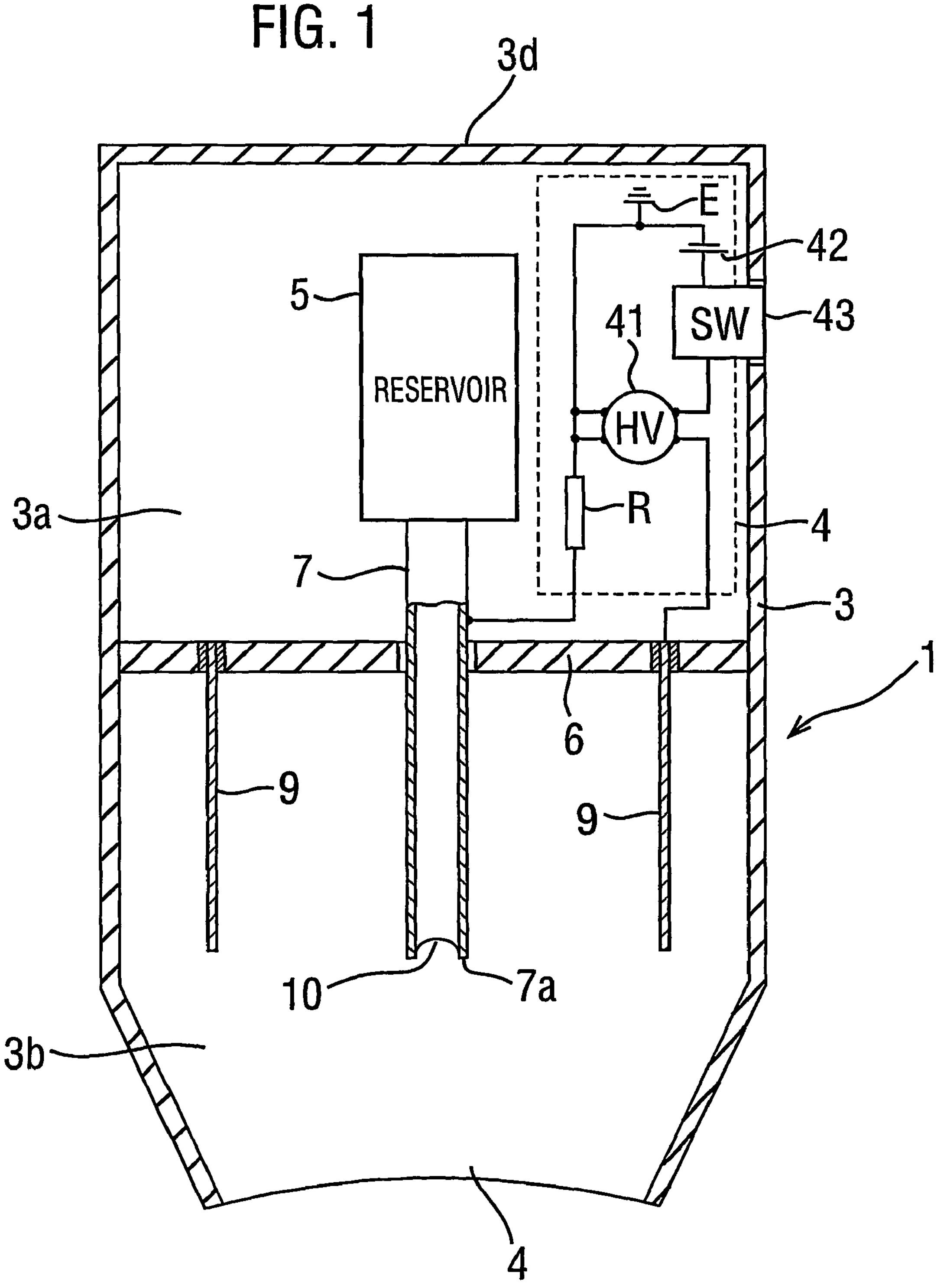
FIG. 1 shows a diagrammatic part sectional view of a first embodiment of a device in accordance with the present invention.

Referring now to the drawings, FIG. 1 shows an aroma dispensing device 1 for dispensing liquid droplets comprising or containing a material producing an aroma. The aroma-providing material may, dependent upon the particular application of the device, be any human olfactory system affecting substance such as olfactory suppressants or stimuli such as aromatic oils and perfumes. The aroma producing material may also be a material that affects an animal olfactory system such as, for example, an insect repellant or attractant.

The device 1 comprises a housing 3 made of an electrically insulative material such as a plastics material. The device 1 has an outlet 4 through which aroma carrying liquid droplets are dispensed in use. The device 1 shown in FIG. 1 is intended to be mounted on a wall or other generally vertical surface so that the outlet 4 is lowermost.

The housing 3 has an internal electrically insulative wall 6 which separates first and second chambers 3*a* and 3*b*. The first chamber 3*a* accommodates control circuitry 4 for controlling operation of the device and a reservoir 5 for containing a supply of the liquid to be dispensed. The reservoir 4 is connected to an electrically conductive capillary tube 7 which extends through the wall 6 into the second chamber 3*b* to enable liquid to be supplied from the reservoir 5 through the capillary tube 7 to a comminution or dispersion site 8 adjacent to an outlet 7*a* of the tube 7.

One or more discharge electrodes 9 are supported by the insulative wall 6 so as to extend within the second chamber 3*b*. Although FIG. 1 shows two discharge electrodes 9, there may be only one discharge electrode or three or more discharge electrodes arranged around the circumference of the capillary tube 7.

The control circuitry 4 comprises a high voltage generator 41 powered by a battery 42 having its positive terminal coupled to the high voltage generator via a switching circuit (SW) 43. The high voltage generator 41 acts to multiply the voltage supplied by the battery 42 to provide a voltage sufficient to generate the electric field required to achieve comminution of liquid issuing from the outlet 7*a*. The high voltage generator may be an electromagnetic converter such as manufactured by Brandenburg Astec Europe, Stourbridge, West Midlands, DY8 4PG, United Kingdom or any other suitable high voltage generator capable of being powered by a battery or similar power source. Other possible high voltage generators would be a piezoelectric high voltage source. Also, at least in some circumstances, the battery may be replaced by a mains supply plus an ac/dc transformer. The conductive capillary tube 7 is connected via a resistance R to the earth terminal of the high voltage generator 41 while the discharge electrode(s) 9 are connected to the high voltage (which may be positive or negative with respect to earth) supplied by the high voltage generator 41.

The switching circuitry 43 may consist of a simple mechanical switch such as a push or rocker button manually updated by a user or may consist of an electrically activated switch such as a relay or an electronic switch. In the latter case, the switching circuitry 43 may include timer circuitry to enable the switch to be opened and closed at a time to be set by the timer circuitry. As another possibility, the switching circuitry 43 may include a communications interface to enable remote control of the switching on and off of the device 1. For example, the communications interface may comprise a wireless communications interface, for example, a radio frequency interface operating in accordance with, for example, the BlueTooth protocol or an infrared communications interface or, for example, a cable or wired interface such as an RS232 interface.

When the switching circuitry 43 is operated to activate the high voltage generator 41, the voltage between the electrically conductive capillary tube 7 and the discharge electrode (s) 9 creates a strong electrical field in the vicinity of the outlet 7*a* causing charge to be induced at the meniscus 10 of the liquid within the capillary tube 7. As is known in the art, this causes the liquid surface tension to break down and an electrically charged dispersion of droplets of substantially nearly all the same size (a "monodispersion") is formed which is electrically discharged by ions generated by the discharge electrode(s) 9.

As noted above, the electrically conductive capillary tube 7 is connected to electrical earth (ground) E by the resistance R. As will be explained below, this provides an auto equilibrating effect and reduces the current/voltage gradient characteristics of the device so that it is not necessary to raise significantly the potential difference between the electrically conductive capillary tube 7 and the discharge electrode(s) 9 to achieve a higher discharge ion current. This is advantageous because increasing the potential difference would, in practice, cause the discharge ions to interfere with the electric field generation process leading to sporadic emission and unpredictable performance because, in practice, the number of discharge ions collected by the capillary tube 7 rises very sharply with only a slight increase in electric field strength leading to instability between the electric field and surface tension forces.

In operation of the device 1 shown in FIG. 1, any ions impacting on the capillary tube 7 give up their charge to the capillary tube 7 and this charge leaks away through the resistance R to the reference potential (in this case the electrical earth E). This reduces the potential difference between the dispersion site 8 and the discharge electrode(s) 9 so that the ions from the discharge electrode(s) 9 are less attracted to the dispersion site 8 and may be redirected towards an alternate target such as, for example, housing 3 or a specially provided target (not shown). This enables ion production to be increased by increasing the potential on the discharge electrode(s) 9 without the ions detrimentally affecting the electrical field dispersion.

Figure 2:
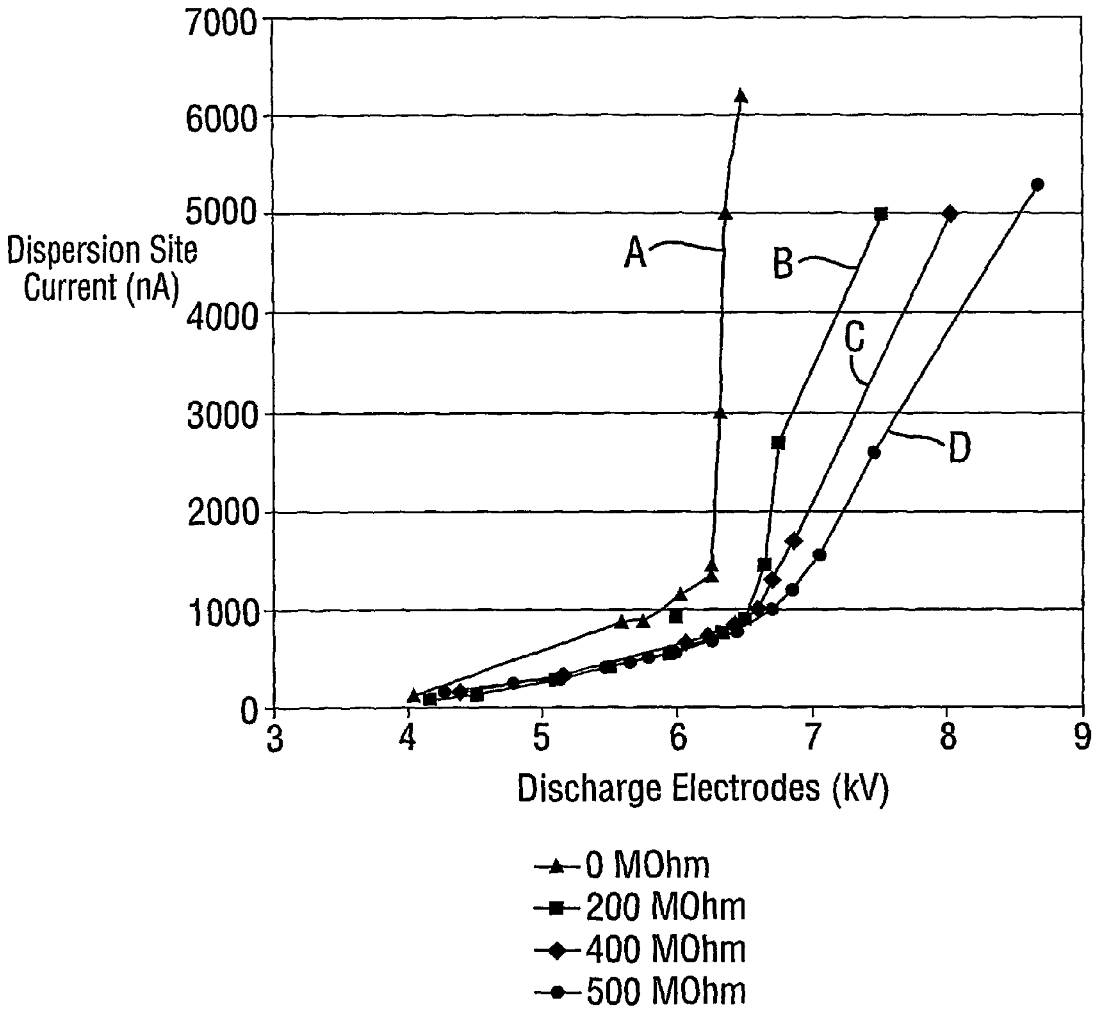
FIG. 2 shows a graph of dispersion site current in nanoamperes against discharge electrode(s) voltage in kilovolts for the device shown in FIG. 1.

FIG. 2 shows a graph of dispersion site 8 current in nanoamperes (nA) against discharge electrode(s) 9 voltage in kilovolts (kV) for experiments carried out using a device having the structure shown in FIG. 1 with a metal capillary tube 7 having an external diameter of 500 micrometers and four discharge electrodes 9 equi-angularly spaced around the capillary tube 7 on a circle 20 millimetres in diameter so that, as shown in FIG. 1, the discharge electrodes 9 extend parallel to the capillary tube 7. The reservoir 5 was filled with an aromatic oil and provided with an air bleed hole (not shown) to give a pressure head of 10 millimetres. As shown in FIG. 1 the arrangement was such that the discharge electrode(s) 9 were connected to the high voltage terminal of the high voltage generator 41 while the metal capillary tube 7 was connected via the resistance R to the electrical earth E. The resistance R used was a variable resistance enabling measurements to be made in the range from 0 to 500 Mega Ohms (MOhms). The electrical current captured at the dispersion site 8 was measured using an ammeter for resistance R values of 0 Mega Ohms, 200 Mega Ohms, 400 mega Ohms and 500 Mega Ohms and, in each case, the voltage applied to the discharge electrode(s) 9 was increased from a value of approximately 4 kilovolts to a value approaching 9 kilovolts. Lines A, B, C and D in FIG. 2 show the results obtained where the resistance is 0, 200, 400 and 500 Mega Ohms respectively. As can be seen by comparing these lines, the value of the series resistance R makes a significant difference to the current captured by the dispersion site 8. Thus, when the resistance R is omitted, i.e. is zero, then, as shown by line A, the dispersion site 8 current increases gradually as the discharge electrode voltage is increased from 4 to 6 kilovolts, and soon after the discharge electrode voltage exceeds 6 kilovolts the discharge site 8 current increases dramatically with increasing voltage so that the gradient of the line A is virtually infinite. However, as can be seen by comparing lines A, B, C and D, as the value of the resistance R is increased, the break point or "knee" at which the dispersion site current starts to increase dramatically softens. The increase in dispersion site current with discharge voltage becomes markedly less rapid after the break point and, moreover, moves to a higher voltage with increase in the value of the resistance R so that when a resistance R having a value of 500 Mega Ohms is used, a discharge electrode voltage of about 6.8 kilovolts can be used. In contrast, when the resistance R is omitted, then in order to avoid runaway of the dispersion site current, the voltage applied to the discharge electrode should ideally be below 6 kilovolts. The fact that the voltage applied to the discharge electrodes 9 can safely be increased to about 6.8 kilovolts using a resistance R of 500 Mega Ohms enables the discharge electrodes to generate more ions which helps to ensure that all of the electrically charged dispersion is electrically discharged, thereby significantly reducing the possibility of the aroma carrying droplets landing on surfaces within the device such as, for example, the discharge electrodes 9. Furthermore, the increased ionic wind provided by the ions generated by the discharge electrodes 9 helps direct the dispersion towards the outlet 4 and away from the device, so reducing the possibility of the aroma-providing droplets landing on or in the vicinity of the device.

Because this arrangement allows a high discharge ion current, the dispersion of aroma containing liquid droplets can have a very high specific surface, that is the droplets can be relatively small, so keeping the amount of aroma dispersed at any one time to a minimum around the olfactory threshold detection level even though the charge to mass ratio of the individual droplets will be very high (approximately 0.1 to 1 coulombs per kilogram) which, if the dispersion could not be readily and reliably discharged, would result in the very low mass (less than approximately 10-12 kilograms for example) droplets migrating readily and landing on nearby conducting surfaces. This should reduce any residual deposit of the dispersion inside or near the device which would otherwise continue to give off an aroma (which may be degrade with time) despite the fact that the device has been switched off.

Accordingly, the device 1 enables production of the aroma to be stopped automatically and virtually immediately once the device is switched off. The fact that deposition of the dispersions droplets on or in the vicinity of the device is avoided or at least reduced also has the advantage of ensuring that the device itself maintains a clean appearance and does not become coated with droplets of the dispersion which may otherwise soften or discolour the material forming the housing.

Figure 3:
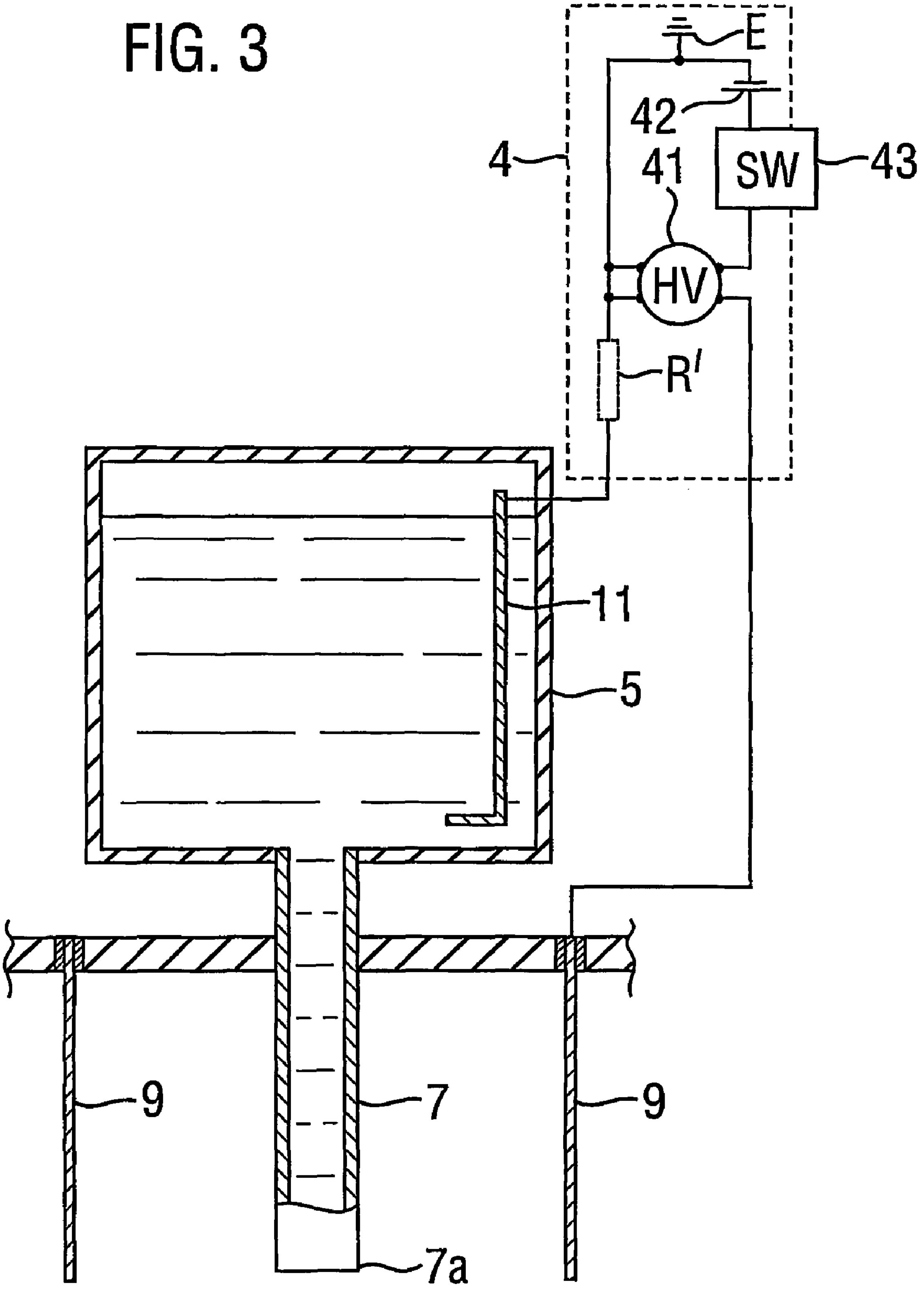
FIG. 3 shows a diagrammatic part sectional view of part of a device embodying the present invention to illustrate a modification of the device shown in FIG. 1.

In the arrangement shown in FIG. 1, the resistance R is provided as a physical resistor component. As another possibility, if the liquid being used is sufficiently resistive, then the liquid itself may provide the resistance R. This may be achieved by, for example, forming the capillary tube 7 of an electrically insulative material apart from the point at which connection is made to the control circuitry 4. FIG. 3 shows a part sectional view of part of a modified form of the device 1 to illustrate another way of providing the resistance R using the liquid. As shown, the electrically conductive capillary tube 7 is again coupled to an electrically insulative reservoir 5 but, in this case, the connection between the control circuitry 4 and the dispersion site 8 is not provided via a direct connection to the electrically conductive capillary tube 7 but rather by way of an electrode 11 extending into the reservoir 5 so that the path to the outlet 7*a* and thus the dispersion site is provided at least partly through the liquid within the reservoir 5 and the capillary tube 7. In all other respects this device is the same as that shown in FIG. 1 except that the resistance R is not provided in the control circuitry 4. If the liquid is not sufficiently resistive, then the series resistance of the liquid may be supplemented by a resistor R' (shown in dashed lines in FIG. 3) so that the combined series resistance of the resistor R' and the liquid path to the outlet 7*a* is comparable to the resistance provided by the resistor R in FIG. 1.

Figure 4:
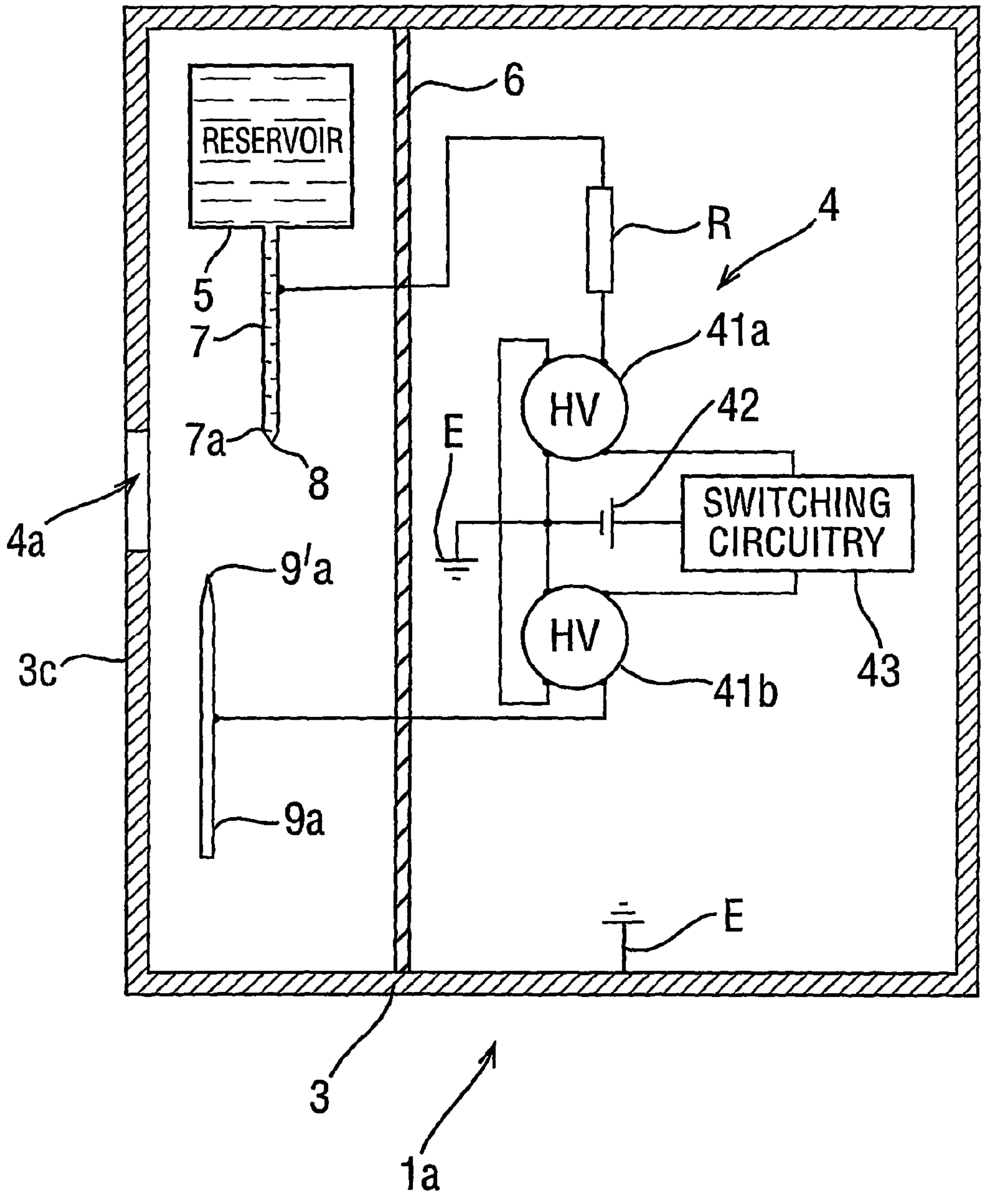
FIG. 4 shows a diagrammatic part sectional view of another embodiment of a device in accordance with the present invention.

FIG. 4 shows a diagrammatic part sectional view of another example of a device 1*a* embodying the invention. The device 1*a* shown in FIG. 4 differs from the device 1 shown in FIG. 1 in that the outlet of the device 1*a* is provided as a circular aperture 4*a* in an electrically conductive sidewall 3*c* of the housing 3 with the aperture 4*a* being arranged so that the dispersion site 8 is approximately level with the uppermost point on the perimeter of the aperture 4*a*. In this embodiment, a single discharge electrode 9*a* is provided and arranged so as to be parallel to and extend in the opposite direction from the capillary tube 7. The discharge electrode 9*a* is arranged so that its sharp end 9'*a* is positioned just below the bottom point of the aperture 4*a*, in this example 1 to 2 millimetres below to the bottom point of the aperture 4*a*.

In this example, the control circuitry 4 has opposite polarity high voltage generators 41*a* and 41*b*. The dispersion site 8 is connected to one of the high voltage generators 41*a* via the resistor R which may be a discrete component as described above with reference to FIG. 1 or may at least partly be provided by a resistive path through the liquid as described above. The discharge electrode 9*a* is in this case connected to the other high voltage generator 41*b* and the electrically conductive side wall 3*c* of the housing is connected to the electrical earth E. For simplicity, the entirety of the housing may, in this example, be electrically conductive because it is electrically earthed. The switching circuitry 43 is again coupled between the positive terminal of the battery 42 and the high voltage generators 41*a* and 41*b* power inputs.

When the switching circuitry 43 is operated to activate the high voltage generators 41*a* and 41*b*, the housing 3 is connected to electrical earth, whilst the dispersion site 8 is raised to a high voltage of one polarity by the high voltage of the generator 41 and the discharge electrode 9*a* is raised to a high voltage of the opposite polarity by the other high voltage generator 41*b*. Typically, the voltage applied to the capillary tube 7 may be +4.7 kilovolts while the voltage applied to discharge electrodes 9*a* may be −3.7 kilovolts.

In this case, the electric field generated at the dispersion site 8 again causes an electrically charged dispersion of aroma-providing liquid droplets to be produced which are discharged by the ions generated by the discharge electrode 9. Ions from the discharge electrode 9 that are not used to discharge the aroma-providing liquid droplets, travel not only towards the dispersion site 8 but also towards the earthed side wall 3*c* so creating an air flow which funnels the aroma-providing dispersion out through the aperture 4*a*. It will be appreciated that where the components of the device 1*a* are housed within a larger structure, then the device will not necessarily be provided with its own housing and the electrically conductive side wall 3*c* could be provided by an earthed electrode which acts to draw the excess ions generated by the discharge electrode 9*a* in the desired direction to entrain the aroma-providing droplets.

Experiments carried out with a device 1*a* having the structure shown in FIG. 4 have shown the device to be virtually 100 percent efficient, that is virtually all of the aroma-providing dispersion exits the device 1*a* leaving little or no aroma-providing dispersion in or around the device. This enables switching on and off of the aroma to be accurately controlled and avoids any odour or degraded odour lingering on or around the device 1*a* due to undesired deposition of aroma-providing droplets.

Although FIG. 4 shows the discharge electrode 9 as being arranged parallel to the capillary tube 7 this need not necessary be the case and for example, the discharge electrode 9*a* may be arranged at a slight angle with respect to the capillary tube 7 so that it is angled either towards or away from the exit aperture 4*a*. In this arrangement because the discharge electrode 9*a* funnels the dispersion towards the exit 4*a*, the resistance R is less important and may be omitted.

In the above described embodiments the reservoir 5 may be formed as a rigid body provided with an air bleed hole (not shown) to allow the liquid level within the reservoir 5 to fall as the liquid is used up during use of the device. As another possibility, the reservoir 5 may be provided as a flexible or collapsable component that collapses as the liquid is used up. This latter arrangement has the advantage that is not necessary to allow air (which may be otherwise have a deleterious effect on the aroma producing liquid) to enter the reservoir 5.

Figure 5:
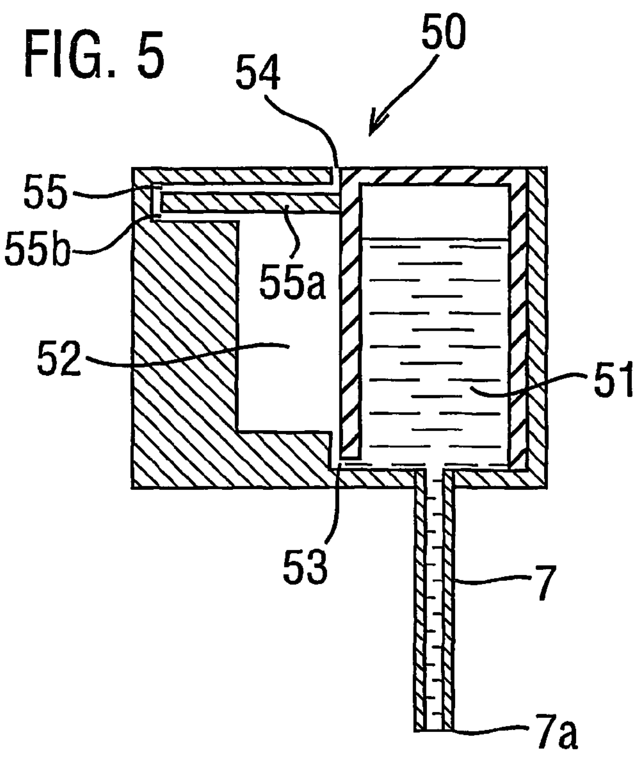
FIG. 5 shows a diagrammatic cross sectional view of one example of a liquid reservoir and supply tube combination suitable for use in a device embodying the present invention.

FIG. 5 shows a diagrammatic cross sectional view of another example of a reservoir 50 and capillary tube 7 combination that may be used in a device 1 or 1*a* embodying the invention. In this example, the reservoir 50 comprises a housing defining a first chamber 51 containing the liquid to be used and coupled to the capillary tube 7 and a second or air chamber 52 connected to the liquid chamber 51 via an air channel 53 located below the liquid level within the liquid chamber 51. As shown, the air channel 53 is provided at the bottom of the liquid chamber 51. The air chamber 52 has an air vent 54 in its uppermost wall 52*a* so as to enable air to enter the air chamber 52. To avoid liquid exiting the reservoir via the air chamber 52 and to avoid undue evaporation of the aroma-providing liquid, the air vent 54 communicates with the air chamber 52 via a tortuous narrow path 55 defined in the example shown by a wall 55*a* projecting into the air chamber and a cooperating recess 55*b* in the side wall of the air chamber.

As in the above described embodiments, liquid is retained within the liquid reservoir 51 by the surface tension within the capillary tube 7. This, of course, requires that the dimensions of the capillary tube 7 outlet 7*a* be sufficiently small and, in practice, requires that the external diameter of the outlet 7*a* satisfy the relationship:

$$d<4\gamma/\rho gh$$

where d is the diameter of the dispersion site or outlet 7*a*, γ is the surface tension of the liquid, ρ is the density of the liquid, g is the acceleration due to gravity and h is the head of liquid above the outlet 7*a*.

Typically:

γ=25 Newtons per metre

ρ=0.89 kilograms per litre g=9.81 and h=20 millimetres indicating that d should be less than 573 micrometers. In this example d was chosen to be 300 micrometers to give a margin of error and to allow for any rise in the pressure head h.

The air chamber 52 not only provides a path for air to enter the liquid chamber 51 to replace liquid supplied via the outlet 7*a* but also provides an expansion chamber into which liquid from the liquid chamber 51 can be displaced if the air that is inevitably present in the liquid chamber 51 expands as a result of environmental changes, for example temperature changes. As will be appreciated from the above, any such expansion should not cause liquid to be pushed out of the liquid outlet 7*a* provided that the inequality given above still holds which can be achieved by making the chamber S1 sufficiently wide so that the change in the pressure head h for a given volume expansion is relatively small, so achieving a relatively constant pressure head and thus also the advantage of providing a relatively constant flow.

The narrow and circuitous path 55 to the air vent 54 serves to reduce the possibility of loss of liquid from the reservoir by evaporation which also avoids or at least reduces the problem of stray aromas or solvents emanating from the reservoir 50 when the device is switched off.

Figure 6:
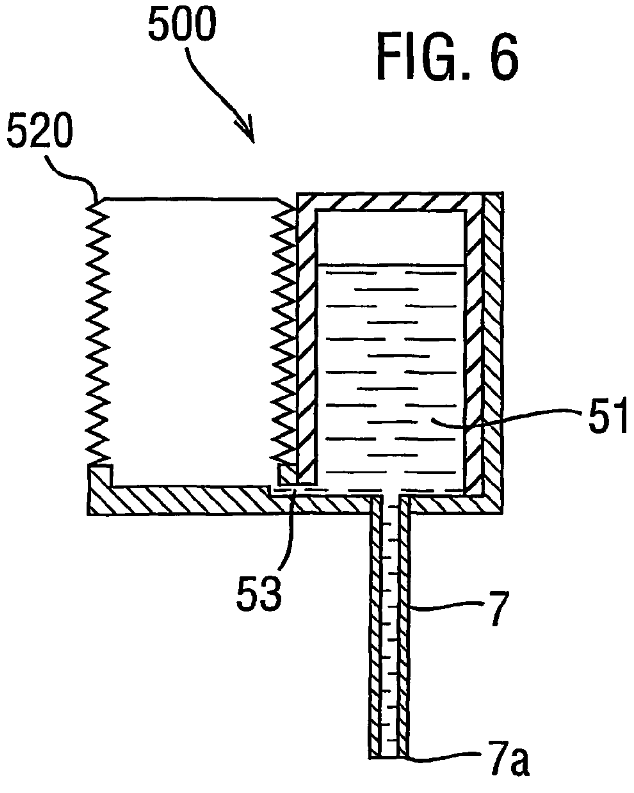
FIG. 6 shows a diagrammatic cross sectional view of another example of a liquid reservoir and supply tube combination suitable for use in a device embodying the present invention.

FIG. 6 shows a cross sectional view similar to FIG. 5 of another embodiment of a liquid reservoir 500 and capillary tube 7 combination for use in a device 1 or 1*a* embodying the invention. The liquid reservoir 500 shown in FIG. 6 differs from the liquid reservoir shown in FIG. 5 in that the rigid air chamber 52 is replaced by a collapsable bag or container 520 which, when fully expanded as shown, holds sufficient air to replace the liquid in the liquid chamber 520 and which has a sufficient volume to allow for air expansion due to environmental changes such as an ambient temperature rise. The flexible or collapsable container 520 can be manufactured from, for example, a thin film of PET or other plastics material. This thin film may be coated in a thin metallic layer to reduce the possibility of diffusion through the flexible wall surface. As another possibility the thin film itself maybe a thin metallic film. The use of the flexible container 520 has the advantage that the flexible container can be completely sealed apart from the communication channel 53 with the liquid reservoir 51 so that there is no air vent via which liquid could evaporate to atmosphere, resulting in undesired and lingering aromas.

There is a small possibility of evaporation of liquid from the liquid outlet 7*a*. Although this will be small in comparison to the liquid flow rate, it is desirable to avoid any such evaporation, however, small, if a very sharp cut off in the supply of the aroma is required.

Figure 7:
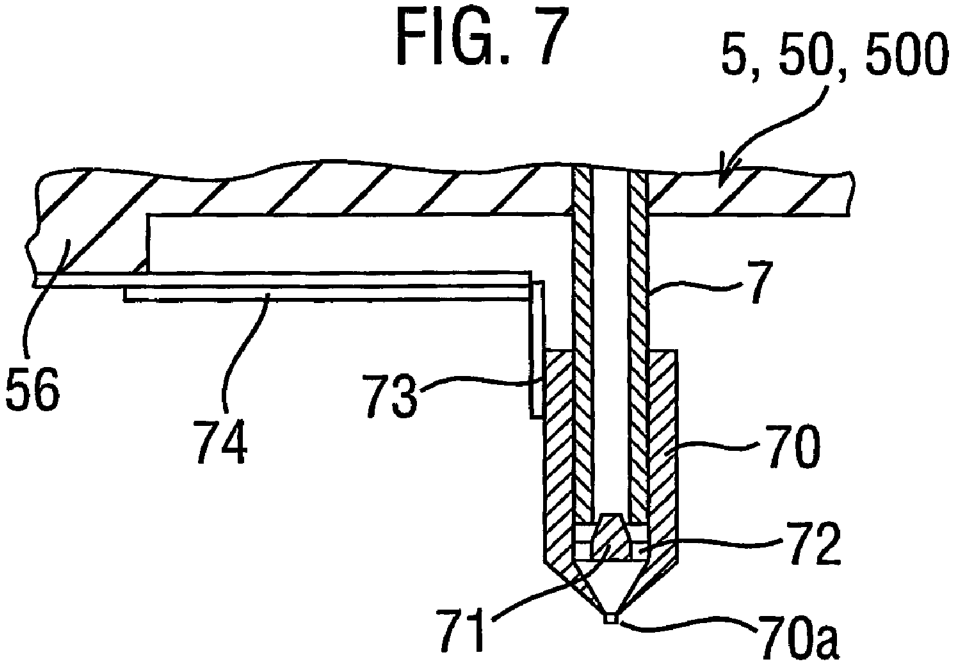
FIGS. 7 and 8 show diagrammatic sectional views of part of the liquid reservoir and supply tube combination shown in FIG. 5 or 6 to illustrate a modification thereof.
Figure 8:
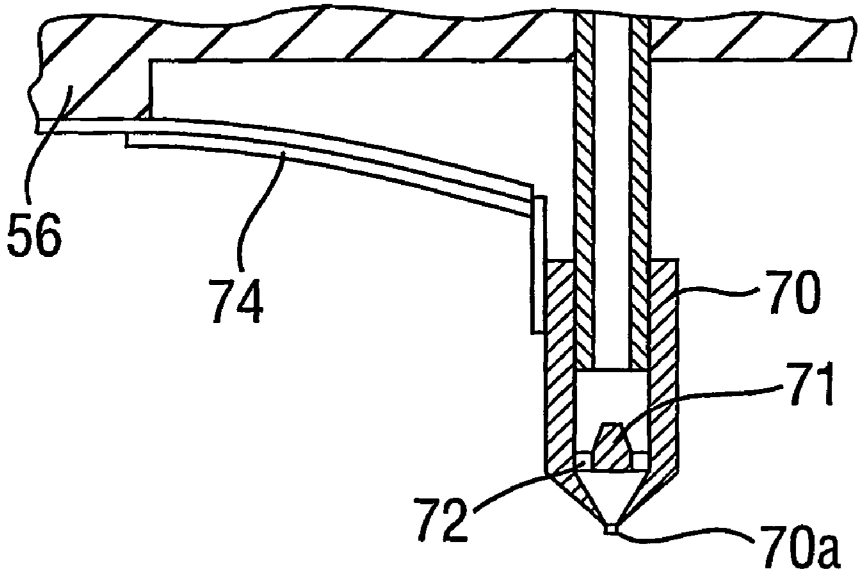

FIGS. 7 and 8 show cross-sectional views of a lower part of the reservoir 5, 50 or 500 and the capillary tube 7 of a further embodiment of a device in accordance with the invention to illustrate one way of avoiding loss of liquid by evaporation from the outlet of the capillary tube. In this example, an electrically operated valve is provided to close the outlet 7*a* when the device is not in use. As shown in FIGS. 7 and 8, the valve comprises a cap member 70 which fits over the lower end of the capillary tube 7 so that the dispersions site 8 is provided by an outlet 70*a* of the cap member 70 rather than the outlet of the capillary tube 7. A valve member 71 is supported within the cap member 70 on support ribs 72 arranged at spaced apart locations around the periphery of the valve member. The cap member 70 is coupled via a connection rod 73 to one end of a piezoelectric bimorph 74, the other end of which is fixedly secured to a fixing post 56 provided on the reservoir. Although not shown, the piezoelectric bimorph 74 is electrically coupled to the voltage source 42 when the switching circuitry 43 is operated to activate the device 1.

FIG. 7 shows the valve in its closed condition with the valve member 70 blocking the outlet 7*a* of the tube 7. When the switching circuitry 43 is operated to activate the device, an electrical signal is applied to the piezoelectric bimorph 74 causing it to bend downwardly so moving the cap member 70 downwardly to the position showing in FIG. 8 so that the valve member 71 is out of contact with the outlet 7*a* of the tube 7 and allows liquid to flow out of the tube 7 past the ribs 72 and to the dispersion site 8 provided at the outlet 70*a* of the cap member 70.

Other forms of electrically operable actuating members for moving the valve member 70 between the open and closed conditions may be used, for example an electromagnetic solenoid may be used. Also, other valve configurations can be envisaged. For example, the valve seat may be provided on a rod which extends within the tube 7 rather than supported on an external cap member 70. The use of an external cap member has, however, the advantage of facilitating connection to the electrical actuator.

In the embodiments shown in FIGS. 5 and 6, the liquid chamber 51 may be a permanent part of the reservoir. However, as another possibility the liquid chamber 51 may be provided as a separable component enabling the liquid reservoir to be replenished by replacing an empty liquid chamber 51 with a fresh, filled liquid chamber.

FIG. 9*a* shows a cross-sectional view through a replacement liquid chamber 510. As can be seen, the liquid chamber 510 has an open end which is closed by a frangible seal 510*a*, for example a metal foil heat sealed to the remainder of the chamber. FIG. 9*b* shows a modified form of the liquid reservoir shown in FIG. 5 adapted to receive such a replacement liquid chamber 510. This reservoir 50*a* differs from the reservoir 50 shown in FIG. 5 in that the liquid chamber 51 is omitted and the air chamber is coupled to a liquid chamber receiving section 50*b* connected to the capillary tube 7. As can be seen from FIG. 9*b*, the lower floor of the reservoir 50*a* is provided with one or more projections 50*c* which, when the replacement liquid chamber 510 is inverted and inserted into the liquid chamber receiving section, pierce the frangible seal 510*a* to allow liquid to be released from the replacement reservoir 510 and also to allow air from the air chamber 52 to enter the replacement liquid container 510. This arrangement therefore enables replenishment of the device 1 with liquid using a sealed replacement liquid chamber or container which inhibits evaporation of volatile aroma-providing liquid and also inhibits the possibility of spillage of the aroma-providing liquid onto component parts of the device that may be adversely affected by the aroma-providing liquid. The use of such a replacement liquid chamber thus further reduces the possibility of undesired escape of aroma.

The liquid reservoir 500 shown in FIG. 6 may also be modified so as to accept a replaceable liquid chamber.

As another possibility, the liquid chamber 51 may be provided with a needle or like valve enabling replenishment using a syringe.

The liquid reservoir arrangements described above not only reduce liquid loss due to evaporation when the device is not in use but also reduce the possibility of liquid loss due to electric field induced liquid movement and migration when the device is in operation by, in the case of the liquid reservoir shown in FIG. 6, ensuring that the only exit from the liquid reservoir is the dispersion site outlet and, in the case of the liquid reservoir shown in FIG. 5, providing a narrow and tortuous path to the air vent 54 of the air chamber 52.

The present inventors have also found another way of inhibiting loss of liquid by evaporation from the liquid outlet or dispersion site 7*a* that does not require the use of a valve. Thus, the present inventors have found that application of an electric field can be used to cause the aroma-providing liquid to withdraw upwardly into the capillary tube 7. FIG. 10 shows a schematic diagram to illustrate how this may be achieved. This modification may be applied to any of the devices described above. Thus, a dielectric layer 80 is provided on the exterior wall of the electrically conductive capillary tube 7 and an electrode 81 is provided on the dielectric layer 80. In this example, as shown schematically in FIG. 10, switching circuitry 430 is provided to enable switching of the output of the high voltage generator 41 between a connection to the discharge electrode 9 and connection to the electrode 81 with the arrangement being such that, when the device is activated to enable supply of an aroma, the switching circuitry 430 couples the high voltage to the discharge electrode 9 and the capillary tube 7 to electrical earth while, when the device is deactivated, the switching circuitry 430 couples the high voltage to the electrode 81. It will be appreciated that, in this arrangement, the high voltage generator 41 is always coupled to the battery 42. A separate manually operable switch 43*a* may be however provided to enable disconnection of the high voltage generator from the battery.

When the voltage supplied by the high voltage generator is applied to the electrode 81, liquid within the capillary tube 7 rises upwardly within the tube away from the outlet 7*a* so reducing the possibility of evaporation at the outlet. However, once the high voltage is disconnected from the electrode 81, the level of the liquid within the capillary tube 7 falls again so enabling liquid to be supplied to the outlet 7*a* for dispersal of the aroma. It will be appreciated that the arrangement shown in FIG. 10 could also be applied to the narrow air channel or path 55 shown in FIG. 5 by forming at least part of the wall of the air channel of an electrically conductive material and providing a dielectric layer 80 and electrode 81 coupled to the high voltage generator via the switching arrangement described above.

In the above described embodiments, the liquid outlet is located below the reservoir 5 enabling gravity feed of liquid from the reservoir 5 to the liquid outlet 7*a* or 70*a*. However, there may be circumstances where it is desirable to mount the device in a different orientation so that, for example, the top wall 3*d* of the housing 3 shown in FIG. 1 forms a base of the device enabling the device to be sat on a tabletop or like surface. In such circumstances, a pumping arrangement may be required to ensure adequate supply of liquid to the liquid outlet. This may be achieved by, for example, providing a conventional electrically operable pump in the liquid supply from the reservoir 5 with the pump being coupled to the voltage source 42 via the switching circuit 43 such that operation of the switching circuitry 43 to activate the device also activates the pump. Any suitable form of pump may be used, for example the zeta pump described in International Application Publication No. WO94/12285 or the electric field pump described in European Patent No. 29301. The use of such pumps enables the same voltage to be used both for generating the electric field to cause comminution and for pumping. The use of the zeta pump also has the added advantage that the pump acts as a valve to hold the liquid away from the liquid outlet 7*a* until required.

In the above described embodiments, the capillary tube 7 is made of an electrically conductive material. This avoids or at least reduces the possibility of electro-osmotic migration of liquid along the capillary tube which might otherwise occur if a capillary tube made of a material such as mica was used. Such electro-osmotic migration of liquid would result not only in liquid being deposited within the device where it may accumulate and produce undesired odours or aromas but also the possibility that the liquid may migrate all the way to the discharge electrode(s) 9 providing a low resistance path between the capillary tube 7 and the discharge electrode(s) 9 which may lead to a supply voltage drop and malfunction.

In addition to the use of an electrically conductive capillary tube 7, unwanted migration of liquid within the device may be avoided or at least reduced by appropriate design of the capillary tube 7 and discharge electrode(s) 9 arrangement so that the radial electrical field discourages migration of liquid along the capillary tube. FIG. 11*a* illustrates the electric field pattern resulting from a capillary tube 7 and discharge electrode 9 arrangement which would induce liquid migration up the capillary tube 7 whilst FIG. 11*b* shows a capillary tube 7 and discharge electrode 9 configuration that ensures that the regular electric field around the capillary tube 7 is strongest at the outlet 7*a* or dispersion site 8 and becomes weaker away from the dispersion site, so inhibiting migration of liquid along the capillary tube.

FIG. 12 shows a diagrammatic part cross-sectional view of another embodiment of a device in accordance with the present invention for generating and controlling the emission of aromas into a space.

The aroma dispensing device 1*b* again has a housing made of an electrically insulative material such as a plastics material. The device has an outlet 400 through which aroma carrying or scented vapour is dispensed in use. Again, the device is intended to be mounted on a wall or other generally vertical surface so that the outlet 400 faces away from the wall or to be supported on a surface such as a table or the like. The housing has, has in the embodiment described with reference to FIG. 1, an internal electrically insulative wall which separates first and second chambers 3*a* and 3*b*. The first chamber 3*a* accommodates control circuitry 4 for controlling operation of the device and a reservoir 5 for containing a supply of liquid to be dispensed. The reservoir is again connected to an electrically conductive capillary tube which extends through the wall 6 into the second chamber 3*b* to enable liquid to be supplied from the reservoir 5 through the capillary 7 to a comminution or dispersion site 8 adjacent to an outlet 7*a* of the tube 7.

A collection device 90 is supported on a base 3*c* of the housing so as to be opposed to the outlet 7*a*. As shown, the collection device 90 comprises a bulbous receptacle 92 formed of an electrically insulative material. The bulbous receptacle 92 has an elongate neck portion 92*a* within which extends an electrically conductive collection electrode 91 which is coupled via a wire extending through a channel provided by a double walled portion 3*d* of the second chamber to the earth terminal of the high voltage source 41. The collection device 90 is positioned so that the opening 90*a* of the neck 92*a* is opposed to, as shown actually aligned with, the outlet 7*a* of the capillary tube 7. As shown, the outlet 400 is offset from a line between the outlet 7*a* and the collection electrode 91.

In this example, the receptacle 92 is generally spherical having an elongate neck. This, however, need not necessarily be the case and any convenient shape of receptacle may be used.

In this example, the receptacle 92 contains an odour or aroma absorbent material 93 such as activated charcoal. Other techniques for inhibiting emmission of aroma from the collection receptacle may be used.

Portions 94 and 96 of the housing of the device may be designed to be removable (for example these portions may be snap-fitted or screw-threaded into the remainder of the housing) to enable the collection device 92 be removed from the housing.

A flow directing device 95 is mounted to a part of the inner wall of the second chamber 3*b* so as to enhance flow in a direction toward the outlet 400. The flow director 95 is powered via the battery 42 or the high voltage source 41, as appropriate. However, for convenience, the connections between the flow director 95 and the power supply are not shown in FIG. 12. The flow director may be an air blower or air circulation device 4 causing a flow of air towards the outlet 400. As another possibility, the flow director may be a sharp point or other electrode coupled to the high voltage source 41 to provide an ion wind towards the outlet 400.

In operation of the device shown in FIG. 12, aroma-providing liquid from the reservoir 7 is subject at the outlet 7*a* to an electric field which causes comminution of the liquid to form electrically charged droplets. The resulting massive increase in the liquid specific surface area causes a very rapid evaporation of aroma-providing or scented vapour into the immediate vicinity. This scented vapour rapidly diffuses and, by virtue of the flow director 95, is directed towards the outlet 400 from which the scented vapour will diffuse into the local environment.

The electrically charged droplets (minus the vapour that has evaporated into the surroundings) are collected, by virtue of inertia and the electric field between the outlet 7*a* and the collection electrode 91 in the receptacle 92 where any remaining volatile aromatics carried by the droplets are adsorbed by the activated charcoal 93 or similar material.

The aroma dispersing device described with reference to FIG. 12 thus enables the scented vapour to be dispersed by the device and the remaining oily droplets to be collected so that the generation of unwanted oil residues on surfaces near or within the device is avoided to enable continuous efficient operation and also so that unpleasant smells or aromas that may arise if the aromatic oil degrades or breaks down over time can be avoided or inhibited. This device should also reduce the possibility of persons standing near the device inhaling oily droplets. In the above described example, the receptacle 92 contains an aroma absorbing material such as activated charcoal. As another possibility, the aroma absorbing material may be omitted and the collection receptacle 92 designed so as to minimise evaporation from the collected oily droplets. In this latter case, the material collected in the receptacle 92 may be removed for disposal or possibly may be recycled by adding further aroma-providing compounds or materials to the collected material and returning that material to the reservoir 5.

The device described with reference to FIG. 13 enables precise control over the timing of emission and intensity of the aroma or smell emitted by the device because of the collection of the oily droplets following the initial evaporation of the volatile aroma or scent providing material.

In the above described example, a flow director is used to direct the evaporated aroma-providing or scented vapour towards the outlet 400. In some cases, however, the flow director may not be necessary and can be omitted.

The liquid reservoirs and chambers described above with reference to FIGS. 5, 6, 7, 8, 9*a* and 9*b* may be used in the device described above with reference to FIG. 12.

As mentioned above, a device embodying the invention may be wall mounted, or supported on a horizontal surface such as a table, shelf or the like. In addition, the device may be sized so that it can be held in the hand or carried around in a handbag, pocket or the like.

A device embodying the invention may be used, as discussed above, to dispense an aroma into a room, space or other environment. In addition, a device embodying the invention may be used to direct the aroma onto an associated object. For example, a device embodying the invention may be used to supply an aroma or smell to artificial flowers so that the smell of the artificial flowers imitates that of the corresponding real flowers. In addition, a device embodying the invention may be used, for example, in a shop or the like to provide an artificial display of foodstuffs with a smell imitating that of the corresponding real foodstuff.

FIG. 13 illustrates very diagrammatically the use of a device 1" embodying the invention to provide artificial flowers F with a smell imitating that of the corresponding real flowers. The device 1" may have any of the forms described above and is incorporated within a vase or other container 200 holding the flowers F so that, as shown, when the device 1" is activated, liquid droplets LD (or aroma-providing or scented vapour where the device is of the type shown in FIG. 12) emerging from the outlet 4 are directed onto an absorbent wick-like material such as, for example, blotting paper or cotton wadding. In the arrangement shown, the wick-like material is provided as a pad or mat 201 near the neck of the vase 200. Alternatively or additionally, the flowers themselves, for example their stems, may be formed at least partially of a wick-like material.

As discussed above, the device may be manually activated or the switching circuitry 43 may include a conventional timing device which causes the device 1" to be activated periodically to dispense aroma or aroma-providing liquid droplets onto the flowers or the pad 201.

Each of the devices described above has a single dispersal site or outlet 7*a* or 70*a*. However, the device may be provided with more than one dispersal site with each site being arranged to deliver a different aroma. A timing mechanism may be provided so that, for example, the different aromas are delivered at different times. This would enable, for example, different aromas or perfumes to be delivered into a room or other space or onto a substrate or object such as a vase of artificial flowers or artificial foodstuffs at different times. Different dispersal sites may also be activated simultaneously to provide, for example, a mixture of aromas where, for example, a vase of artificial flowers represents a mixture of different real flowers.

FIG. 14 shows a block diagram of an aroma delivery apparatus 300 incorporating a plurality of devices 100 in accordance with the present invention. Each of these devices may have any of the configurations described above. It will, of course, be appreciated that in this arrangement each device need not necessarily have its own housing. The apparatus 300 comprises a microprocessor or microcontroller 301 having associated memory 302, a user interface 303 such as a control panel or a touch sensitive screen and a number of devices 100. The switching circuitry 43 of each device 100 is coupled to the controller 301 via an appropriate interface so that the controller 301 can control switching on and off of each of the devices 100. Using this apparatus, a user may program, via the user interface 303, the controller 301 to activate the devices 100 in a sequence or pattern determined by the user and at times and for durations also determined by the user. The memory 302 may also contain preset programs defining preset sequences of activation for the devices 100.

The apparatus shown in FIG. 14 may be miniaturised because the reservoirs need only be very small because only a few drops of an aromatic or essential oil are necessary to stimulate the olfactory senses. In addition, the individual devices 100 may share a common battery and common high voltage generators allowing for further miniaturisation. With such miniaturisation the apparatus 300 may be sized so that it can be worn by a user 20, for example on a belt, or clipped to the user's shirt, blouse or other item of apparel 21 as shown in FIG. 15. In this case, the user interface 303 may include a remote control receiver for receiving control signals from another item of equipment to enable the supply of aromas by the apparatus to be controlled by that other item of equipment. The other item of equipment may be, for example, a personal computer enabling, for example, appropriate aromas to be dispensed during the playing of a computer game, or other home entertainment equipment comprising, for example, a video or DVD player, a CD or cassette player, a television, a cinema projector or the like so that the apparatus 300 can delivery aromas in coordination with the output from the item of home entertainment equipment.

As another possibility, the apparatus 300 may be associated with a telephone so that an aroma is generated when the telephone rings. The user interface 303 may also provide for a physical connection via a cable to the item of home entertainment equipment. This would have the advantage that the power source for the apparatus 300 may be located at the item of home entertainment or equipment or in an additional box so making the apparatus 300 itself more simple and less bulky. As another way of programming the device, the apparatus 300 may be provided with a barcode reader 304, see FIG. 14A, that may, for example, be used to scan the barcodes that appear in television program listings so that an aroma-providing dispersion that complements the program being watched may be generated.

The apparatus shown in FIG. 14 may be combined with an item of home entertainment or other equipment in an integrated manner. FIG. 16 shows a perspective view of a clock radio 400 having a radio 401, an LCD display clock 402 and also incorporating apparatus 300 having, in the example shown, four different devices 100 each having a respective aroma outlet port 404. In this case, the user interface or control panel 303 may be used to program alarms in the conventional way and also to program the controller 301 to cause different aromas or combinations of aromas to be dispensed at different times so that, as desired by the user, the user may receive an alarm as either activation of the radio and/or of an inbuilt buzzer in conventional manner and/or by dispersal of one or more aromas. To improve the dispersal of the aromas, the apparatus may be provided with a louvred air inlet 406 and an internal air circulation method (such as an internal fan and/or heater not shown).

As an example, the apparatus 300 may dispense a smell simulating that of coffee or eggs and bacon to wake the user up in the morning or to remind them that it is time for breakfast. Also, a smell or aroma such as a perfume may be delivered into the environment periodically throughout the day so as to improve the smell of the environment or to enhance the mood of the occupant. Because a device embodying the invention enables precise control of the switching on and off of the aroma delivery, different aromas or smells may be provided throughout the day to enable, for example, different alarms for different tasks or appointments to be programmed, without the different aromas adversely interfering with one another. A pre-programmed device may be sold with a CD or video or the like or instructions for programming the device may be provided with a CD or video so enabling a user to be provided with a sequence of aromas or smells complementing the audio or audio visual experience provided by the CD or video.

In each of the examples described above with reference to FIGS. 13 to 16, the devices 100 may be provided as plug-in units to enable a user to replenish or change these at will.

A device embodying the invention may also be incorporated in a motor vehicle 305, see FIG. 14B, possibly being powered from the vehicle battery, and be programmed so as to release a smell or aroma a predetermined period of time after the driver switches on the car ignition so as to alert the driver to the fact that he has been driving for, for example, several hours and to either improve his alertness or to warn him to take a rest.

The surface tension, resistivity and, to a lesser extent, viscosity of aromatic oils can affect their performance and in many cases it is desirable to add a non-aromatic oil or carrier to the aromatic oils to adjust the properties of the aromatic oil so as to facilitate dispersal of the aroma. It is difficult to quantify the properties required for the complementary oil or carrier because this will depend, of course, on the properties of the aromatic oil being used. Generally, however, the resultant viscosity should be under 10 centipoise, although it may still be possible to disperse satisfactorily liquid having viscosities tens of times higher than this although the performance may be less reliable. As a rule of thumb the following equation should yield a positive value for optimum performance.

$$\text{Value}=3277\times(0.734-\text{Log}_{10}(((\gamma-23.95)^{\wedge}2)^{0.5}+((\gamma-29)^2+(\text{Log}_{10}(\rho)-4.54)^2)^{0.5}))),$$

Where $\gamma$ is the surface tension in milli Newtons per metre and $\rho$ is the resistivity in ohm metres of the liquid to be dispersed.

The aroma-providing liquid may be in any suitable form for dispersal, for example, a solution, a melt a suspension, emulsion, microsuspension, microemulsion or gel.

A device embodying the invention may be used, as described above, as an alarm. The device embodying the invention may also be used, in conjunction with appropriate conventional sensors, as an intruder alarm to, for example, alert the owner or occupier of premises to the presence of an intruder or to deter an intruder by releasing an unpleasant odour. A device embodying the invention may also be used to provide an aroma-providing boundary marker to, for example, demarcate a dangerous hazard or attract attention to, for example, a conference stand, advertisement, canteen or building.

A device embodying the invention could be used to send aroma-providing signals to distinguish between different places, or between different functions of places or objects. For example, it could designate by smell or aroma the various food counters in a supermarket, or the retail outlets in a department store. Designer outlets could have customised fragrances to enhance the exclusivity of their brand or product. The aroma-providing signal would then provide an extra element of consistency worldwide for a company, brand, product or individual. A device embodying the invention could similarly be used to provide differentiation by smell or aroma between products, such as between different models of cars.

As described above a device embodying the invention may be used for the personal delivery of dispersions. For example, a user might carry one about their person to fragrance the air wherever they go, such as to improve the smell of their office, car or washroom. Such a device could also be used to personally fragrance clothes if placed in a wardrobe, clothes drawer or closet.

As mentioned above, a device embodying the invention may be used to produce aromas for repelling or attracting animals other than human beings and, for example, the dispensed aroma may be designed to repel insects or to attract insects for separate immobilisation on a sticky strip or to an electrocution grid.

As another possibility, the dispersion could contain insecticides in addition to insect attractants.

A device embodying the invention may be used as an alternative to all commercial aerosol cans and pump sprays that create space sprays and has the advantage that switching on and off of the aroma delivery can be precisely controlled that having any aroma lingering in the environment which might otherwise degrade with time resulting in less desirable aromas or might mix unfavourably with other aromas.

The invention claimed is:

1. An electrohydrodynamic aroma dispensing device, comprising:

means for supplying liquid to an electrically conductive outlet an electrical discharge means;

means for coupling said outlet to a first potential representing a first low magnitude potential and for directly coupling said electrical discharge means to a second, different, higher magnitude potential for causing an electric field to be generated at said outlet to produce a dispersion of aroma-providing droplets from liquid issuing from the outlet and for producing at said electrical discharge means ions to at least partially neutralize an electrical charge from the liquid dispersion, wherein said outlet is coupled to said first potential via a resistance.

2. A device according to claim 1, wherein said coupling means is arranged to couple said outlet to earth.

3. A device according to claim 1, wherein said coupling means is arranged to couple said electrical discharge means to a second potential which is positive with respect to said first potential.

4. A device according to claim 1, wherein said resistance has a value in the range of from approximately 200 Mega Ohms to approximately 500 Mega Ohms.

5. A device according to claim 1, wherein said resistance has a value of approximately 500 Mega Ohms.

6. A device according to claim 1, wherein said resistance is provided by liquid in the liquid supplying means.

7. A device according to claim 1, wherein the electrical discharge means surround or are provided on either side of the liquid outlet.

8. A device according to claim 1, wherein the resistance couples the outlet to the first potential.

9. A device according to claim 8, wherein the resistance comprises a liquid path.

10. A device according claim 8, wherein the resistance is approximately 500 Mega ohms.

11. A device according to claim 1, comprising control means for enabling the device to be activated in a predetermined manner which may be at a predetermined time, periodically or at a user settable time or times or a combination of the aforementioned possibilities.

12. A device according to claim 11, comprising a plurality of supplies of different liquids and means for controlling the generation of an electric field to cause comminution of each of the different liquids at different times.

13. A device according to claim 1, wherein the resistance is greater than 0 ohms.

14. A device according to claim 1, wherein the resistance is a variable resistance.

15. A device according to claim 14, wherein the resistance varies from greater than 0 ohms to 500 Mega Ohms.

16. A device according to claim 1, wherein the resistance comprises a liquid in combination with a resistor.

17. A device according to claim 16, wherein the resistance is variable.

18. A device according to claim 1, comprising a plurality of outlets and a plurality of supplies of different liquids.

19. A device according to claim 18, comprising means for controlling comminution of each of the different liquids at desired times.

20. A device according to claim 1, wherein said liquid supply means comprises a flexible reservoir.

21. A device according to claim 1, wherein said liquid supply means comprises a reservoir including a frangible seal.

22. A device according to claim 1, further comprising a barcode reader.

23. A device according to claim 1, further comprising a receiver to receive control signals from one or more of a personal computer, a video or DVD player, a CD or cassette player, a television and a cinema projector.

24. The device according to claim 1 in combination with a motor vehicle.

25. The device according to claim 1 in combination with one of a radio, a telephone and a cable of a home entertainment item.

26. The device according to claim 1, wherein the device is capable of being sat on a tabletop.

27. The device according to claim 1, wherein the device is capable of being carried about a person.

28. The device according to claim 1, wherein the device includes a liquid containing at least one of an insect attractant and an insecticide.

29. The device according to claim 1, wherein the device includes a liquid containing an insect repellant.

30. The device according to claim 1, wherein the device includes a liquid comprising an olfactory suppressant.

31. The device according to claim 1, wherein the device includes a liquid comprising an olfactory stimulus.

32. An electrohydrodynamic aroma dispensing device, comprising: means for supplying liquid to an outlet; an electrical discharge means; means for coupling said outlet to a first potential representing electrical earth and for directly coupling said electrical discharge means to a second, different potential for causing an electric field to be generated at said outlet to generate a dispersion of aroma-providing droplets using liquid issuing from the outlet and for producing at said electrical discharge means ions to at least partially neutralize an electrical charge from the liquid dispersion, wherein said outlet is coupled to said first potential via a resistance.

* * * * *